United States Patent [19]

Wu et al.

[11] Patent Number: 5,556,769

[45] Date of Patent: Sep. 17, 1996

[54] COUPLED REPLICATION-TRANSLATION METHODS AND KITS FOR PROTEIN SYNTHESIS

[76] Inventors: Ying Wu, 4084 Crystal Dawn La., Apt. 201, San Diego, Calif. 92122; Lyubov A. Ryabova, Apt. 51, Bldg., 29, Microraion V, 142297 Puschino, Moscow Region; Oleg V. Kurnasov, Apt. 104, Bldg. 22, Microraion G, 142292 Puschino, Moscow Region, both of Russian Federation; Igor Y. Morosov, 2, rue de Candolle, 75005 Paris, France; Viktor I. Ugarov, Apt. 77, Bldg., 5, Microraion D, 142292 Puschino, Moscow Region, Russian Federation; Elena V. Volianik, 6 Dawson House, Walden Street, London E1.2BD, United Kingdom; Alexander B. Chetverin, Apt. 238, Bldg. 24, Microraion AB, 142292 Puschino, Moscow Region, Russian Federation; David Zhang, 82-24 165th St., Jamaica, N.Y. 11432; Fred R. Kramer, 561 W. 231st St., Riverdale, N.Y. 10463; Alexander S. Spirin, Apt. 44, Bldg., 27, Microraion V, 142292 Puschino, Moscow Region, Russian Federation

[21] Appl. No.: 294,610

[22] Filed: Aug. 23, 1994

Related U.S. Application Data

[63] Continuation of Ser. No. 71,290, Jun. 2, 1993, abandoned, which is a continuation of Ser. No. 950,805, Sep. 24, 1992, abandoned.

[51] Int. Cl.$^6$ .............................. C12P 21/02; C07H 21/04
[52] U.S. Cl. ......................................... 435/69.1; 536/23.1
[58] Field of Search ........................... 435/69.1; 536/23.1

[56] References Cited

U.S. PATENT DOCUMENTS

| | | | |
|---|---|---|---|
| 4,786,600 | 11/1988 | Kramer et al. | 435/320.1 |
| 5,324,637 | 6/1994 | Thompson et al. | 435/68.1 |
| 5,478,730 | 12/1995 | Alakhov et al. | 435/68.1 |

FOREIGN PATENT DOCUMENTS

| | | |
|---|---|---|
| 0485608A1 | 5/1990 | European Pat. Off. . |
| 0312617 | 3/1993 | European Pat. Off. . |
| 0593757A1 | 4/1994 | European Pat. Off. . |
| 0401369 | 5/1995 | European Pat. Off. . |
| WO88/08453 | 11/1988 | WIPO . |
| WO90/07003 | 6/1990 | WIPO . |
| WO91/02076 | 2/1991 | WIPO . |
| WO91/02075 | 2/1991 | WIPO . |

OTHER PUBLICATIONS

Pratt et al. 1981 Mar, 9(18):4459–4474.
Spirin et al. 1988, Sci. 242:1162–1164.
Kudlicki, et al., "High Efficiency Cell–Free Synthesis of Proteins: Refinement of the Coupled Transcription/Translation System"; Analytical Biochemistry 206, 389–393 (1992).
Kolosov, et al., "Preparative in Vitro Synthesis of Bioactive Human Interleukin–2 in a Continuous Flow Translation System"; Biotechnology and Applied Biochemistry 16, 125–133 (1992).
Endo, et al., "Production of an enzymatic active protein using a continuous flow cell–free translation system"; Journal of Biotechnology, 25 (1992) 221–230.
Axelrod, et al. (1991) "Coliphage Qβ RNA Replication: RNA Catalytic for Single–Strand Release" Virology 184:595–608.
Baranov, et al. (1989) "Gene expression in a cell–free system on the preparative scale" Gene 84:463–466.
Baranov, et al. (1993) "Gene–Expression in Cell–Free System on Preparative Scale" Methods in Enzymology 217:123–142.
Bausch, et al. (1983) "Terminal Adenylation in the Synthesis of RNA by Qβ Replicase" The Journal of Biological Chemistry 258:1978–1984.
Blundell, et al. (1972) "Decay Rates of Different mRNA in E. coli and Models of Decay" Nature 238:46–49.
Domingo, et al. (1985) "The quasispecies (extremely heterogeneous) nature of viral RNA genome populations: biological relevance—a review" Gene 40:1–8.
Domingo, et al. (1978) "Nucleotide Sequence Heterogeneity of an RNA Phage Population" Cell 13:735–744.
Kamen (1975) "Structure and Function of the Qβ RNA Replicase" in RNA Phages (Norton Zinder ed.) pp. 203–234.
Kigawa et al. (1991) "A Continuous Cell–Free Protein Synthesis System for Coupled Transcription–Translation" J. Biochem. (Tokyo) 110:166–168.
Ko (1975) "Possible Mechanism of E. coli Messenger RNA Degradation: Non–Enzymatic Degradation" BioSystems 6:205–208.
Kolakofsky, et al. (1971) "Possible Mechanism for Transition of Viral RNA from Polysome to Replication Complex" Nature New Biology 231:42–46.
Kolakofsky, et al. (1971) "Qβ replicase as repressor of Qβ RNA–directed protein synthesis" Biochem. Biophys. Acta 246:596–599.
Kolakofsky, et al. (1973) "Resynchronization of RNA Synthesis by Coliphage Qβ Replicase at an Internal Site of the RNA Template" J. Mol. Biol. 76:271–284.
Kramer et al. (1978) "RNA sequencing with radioactive chain–terminating ribonucleotides" Proc. Natl. Acad. Sci. USA 75:5334–5338.

(List continued on next page.)

Primary Examiner—George C. Elliott
Assistant Examiner—John S. Brusca
Attorney, Agent, or Firm—William J. Hone

[57] ABSTRACT

Batch and continuous-flow cell-free methods for synthesizing protein wherein translation is coupled with replication of recombinant mRNA by an RNA-directed RNA polyerase, such as Qβ replicase. Transcription of a DNA template to produce the recombinant mRNA can be coupled additionally with coupled transcription-replication-translation methods, both batch and continuous. The invention also includes kits of reagents for synthesizing user-selected proteins according to methods of this invention.

44 Claims, 4 Drawing Sheets

OTHER PUBLICATIONS

Lizardi, et al. (1988) "Exponential Amplification of Recombinant–RNA Hybridization Probes" Bio/Technology 6:1197–1202.

Lomeli, et al. (1989) "Quantitative Assays Based on the Use of Replicatable Hybridization Probes" Clin. Chem 35:1826–1831.

Lucotte, et al. (1993) "Introduction to Molecular Cloning Techniques" VCH Publishers, NY, pp. 123–132.

Melton et al. (1984) "Efficient in vitro synthesis of biologically active RNA and RNA hybridization probs from plasmids containing a bacteriophage SP6 promoter" Nucleic Acid Res. 12:7035–7056 and 7057–7070.

Miele et al., (1983) "Autocatalytic Replication of a Recombinant RNA" J. Mol. Biol. 171:281–295.

Morozov, et al. (1993) "Synergism in replication and translation of messenger RNA in a cell–free system" Proc. Natl. Acad. Sci. USA 90:9325–9329.

Munishkin et al. (1991) "Efficient Templates for Qβ Replicase are Formed by Recombination from Heterologous Sequences" J. Mol. Biol. 221:463–472.

Priano, et al. (1987) "Evolution of the RNA Coliphages: The Role of Secondary Structures during RNA Replication" Cold Spring Harbor Symposia on Quantitative Biology 52:321–330.

Rattan (1990) "Continuous gene expression in vitro: the Spirin system" Tibtech 8:275–276.

Ryabova, et al. (1989) "Preparative synthesis of globin in a continuous cell–free translation system from rabbit reticulocytes" Nucleic Acids Research 17:4412.

Ryabova, et al. "Continuous–Flow Cell–Free Translation, Transcription–Translation and Replication–Translation Systems" in Methods in Molecular Biology (Walker, J. N. ed) in press.

Ryabova, et al. (1994) "Coupled Replication–Translation of Amplifiable Messenger RNA" The Journal of Biological Chemistry 269:1501–1506.

Schleif, et al. (1981) "Practical Methods in Molecular Biology," Springer–Verlag, New York, pp. 56–60 and 161–166.

Spirin, et al. (1991) "Cell–Free Protein Synthesis Bioreactor" in Frontiers in Bioprocessing II (Todd, et al. eds.) American Chemical Society, Washington, D.C. pp. 31–43.

Spirin (1990) "Ribosome Preparation and Cell–Free Protein Synthesis" in The Ribosome: Structure, Function, and Evolution (Hill, W. E., et al. eds.) Amer. Soc. Microbiol., Washington, D.C. pp. 56–70.

Ugarov, et al. (1994) "Expression and stability of recombinant RQ–mRNAs in cell–free translation systems" FEBS Lett. 341:131–134.

Weber, et al. (1972) "Molecular Basis for Repressor Activity of Qβ Replicase" Nature 237:166–170.

Wu, et al. (1992) "Amplifiable messenger RNA" Proc. Natl. Acad. Sci USA 89:11769–11773.

COUPLED REPLICATION-TRANSLATION METHODS AND KITS FOR PROTEIN SYNTHESIS

This is a continuation of U.S. application Ser. No. 08/071,290, filed Jun. 2, 1993, now abandoned which is a continuation of U.S. application Ser. No. 07/950,805 filed Sep. 24, 1992, now abandoned.

The invention relates to protein synthesis in a cell-free system by a method including translation combined with simultaneous replication of recombinant mRNA by an RNA-directed RNA polymerase such as Qβ replicase.

BACKGROUND

RNA-directed RNA polymerases are well known, as are compatible templates that they replicate. Qβ replicase, an RNA-directed RNA polymerase, is known to be compatible with, i.e., to replicate, certain templates exponentially, including MDV-1 RNA, a small, naturally occurring template, and RQ135 RNA. We are aware that Qβ replicase is compatible with and exponentially amplifies recombinant RNAs which comprise a messenger RNA (an mRNA) sequence embedded within the sequence of MDV-1 RNA. We are also aware that for short periods of time the amplified product can be used as a template for the synthesis of its encoded protein in a batch cell-free translation system.

Teachings in the art indicate that the complex and stable secondary and tertiary structures present in full-length recombinant mRNA limit the access of ribosomes to the protein initiation site. Teachings in the art indicate that exponential amplification, which will generate many copies of both plus (+ or sense) and minus (− or antisense) strands of recombinant mRNA, can lead to the hybridization of plus and minus strands to each other over the long term, rendering the plus strands useless for protein synthesis through translation by ribosomes unless the hybridized strands are melted apart prior to use. "Protein" as used herein means the polypeptide synthesized by a ribosome in response to the mRNA that encodes it. Exponential amplification generates both plus and minus strands. Teachings in the art also indicate that replication over a prolonged period, that is, the copying of copies, leads to an accumulation of mutated strands not suitable for synthesis of a desired protein. For these reasons the art suggests that the amplification of recombinant mRNAs by Qβ replicase for use as templates for cell-free translation would not be satisfactory for the production of protein. In particular, one would anticipate that amplification time would have to be kept short (less than one hour), which would be very limiting and not advantageous compared to uncoupled or coupled transcription-translation methods. Furthermore, the art suggests that replication would not be useful in coupled methods, such as transcription-translation, because of the need to melt apart hybridized strands of replicated recombinant mRNA.

It is an objective of this invention to utilize the ability of RNA-directed RNA polymerases such as Qβ replicase to generate large amounts of the recombinant mRNAs to generate templates for protein synthesis while overcoming the three problems, discussed above, taught by the art.

SUMMARY OF INVENTION

We have discovered that coupling the synthesis of compatible recombinant mRNAs by an RNA-directed RNA polymerase, particularly Qβ replicase, to the translation of those recombinant mRNAs by ribosomes in a cell-free translation system unexpectedly provides improved methods to generate functional (biologically active) protein over relatively long periods of time (days). By "cell-free translation system" we mean a mixture comprising ribosomes, soluble enzymes required for protein synthesis (usually from the same cells as the ribosomes), transfer RNAs, adenosine triphosphate, guanosine triphosphate, a ribonucleoside triphosphate regenerating system (such as phosphoenol pyruvate and pyruvate kinase), and the salts and buffer required to synthesize a protein encoded in an exogenously provided mRNA. By "coupled" we mean carrying out recombinant mRNA replication and translation simultaneously in the same reaction vessel, or reactor. This invention includes coupled replication-translation in a cell-free batch process and, importantly, in a cell-free continuous-flow process. Further, the invention includes additionally combining coupled transcription in the same process.

Coupled replication-translation methods according to this invention overcome the limitations caused by the stable secondary and tertiary structures present in full-length recombinant mRNA, because in these coupled systems ribosome binding sites of nascent (partially synthesized) strands are readily available to ribosomes. Coupled replication-translation processes according to this invention do not shut down over long periods of time (days) due to hybridization of plus and minus recombinant mRNA strands. Furthermore, in a coupled replication-translation process carried out over days, the biological function of the protein is not significantly compromised by the accumulation of mutated recombinant mRNA strands.

Transcription (by, for example, a bacteriophage polymerase such as T7 RNA polymerase)-translation methods, including continuous methods, are known in the art. However, transcription by a bacteriophage RNA transcriptase proceeds by a relatively short burst, generating perhaps one-hundred copies of each template DNA molecule, after which transcription of messages practically ceases. Based on private communications from other researchers, we believe that coupled transcription-translation methods are prone to the degradation of the DNA and mRNA which, if encountered, causes cessation or a significant drop-off of protein production. We believe that coupled replication-translation methods according to this invention solve this problem by providing a continuous source of new mRNA and, therefore, significantly improve protein production over long periods of time (days). Continuous methods according to this invention continually generate intact mRNA and give no indication of drop-off of protein synthesis after more than forty hours on stream.

A further aspect of this invention is that by coupling replication of recombinant mRNA strands to their translation, it is predominantly the nascent (partially synthesized) strands which serve as templates for protein synthesis. Because these nascent strands are less structured than full-length strands, they are more accessible to ribosomes and are therefore more efficient than full-length strands as templates for protein synthesis. A batch replication-translation method according to this invention has demonstrated an efficiency of protein production one-hundred percent greater than an otherwise identical batch translation method.

In the methods of this invention, replication is by an RNA-directed RNA polymerase. A number of such replicases known in the art have been isolated, for example, bacteriophage RNA polymerases and plant virus RNA polymerases. In addition, DNA-directed RNA polymerases may serve as RNA-directed RNA polymerases, for example, bacteriophage T7 DNA-directed RNA polymerase. Qβ replicase is particularly preferred. Templates that are replicated by various replicases are also known in the art and can serve as vectors for producing recombinant mRNAs suitable for use in this invention. Vectors that do not have cistrons are preferred. Known templates for Qβ replicase include RQ135 RNA, MDV-1 RNA, microvariant RNA, nanovariant RNAs, CT-RNA and RQ120 RNA. Qβ RNA, which is also replicated by Qβ replicase, is not preferred, because it has cistrons, and further because the products of those cistrons regulate protein synthesis. As vectors we prefer particularly MDV-1 RNA and RQ135 RNA. The sequences of both are published. See Kramer et al. (1978) Proc. Natl. Acad. Sci. USA 75: 5334–5338 (MDV-1 RNA) and Munishkin et al. (1991) J. Mol. Biol. 221: 463–472 (RQ135), both of which are incorporated by reference herein. They can be made in DNA form by well-known DNA synthesis techniques.

Translation according to the methods of this invention is not limited to a particular cell-free translation system. The system may be derived from a eukaryote, prokaryote or a combination. A crude extract, a partially purified extract or a highly purified extract may be used. Synthetic components may be substituted for natural components. Numerous alternatives are available. Many are described in the literature. See Spirin (1990), pp. 56–70 in THE RIBOSOME: STRUCTURE, FUNCTION, and EVOLUTION (eds. Hill, W. E., et al.), Amer. Soc. Microbiol., Washington, D.C., which is incorporated by reference herein. Our preferred cell-free translation system utilizes an S-30 extract from *Escherichia coli*. Suitability of another cell-free translation system for synthesis of a particular protein can be ascertained simply by trying it.

Certain preferred embodiments of this invention include transcription as well as coupled replication-translation. DNA encoding the recombinant mRNA can be, but need not be, in the form of a plasmid. We prefer to use a plasmid and an endonuclease that cleaves the plasmid at or near the end of the sequence that encodes the replicatable RNA in which the messenger sequence is embedded. Linearization can be performed separately or can be coupled with transcription-replication-translation. For some systems non-linearized plasmids without endonuclease may be preferred. Suitability of a particular procedure can be ascertained simply by trying it. Suitable plasmids may be prepared, for example, by following the teachings of Melton et al. regarding processes for generating RNA by transcription in vitro of recombinant plasmids by bacteriophage RNA polymerases, such as T7 RNA polymerase or SP6 RNA polymerase. Melton et al. (1984) Nucleic Acid Res. 12: 7035–7056 and 7057–7070, which are incorporated by reference herein. We do not have any preferred plasmid. However, it is desirable that transcription begin with the first nucleotide of the sequence encoding the replicatable RNA.

Certain preferred methods according to this invention are continuous-flow cell-free methods utilizing coupled replication-translation. Continuous-flow cell-free equipment and procedures for translation or transcription-translation are known in the art and can be adapted to the methods of this invention by changing the composition of materials in the reactor. Several systems and their methods of operation are reviewed in Spirin, A.S. (1991) pages 31–43 in FRONTIERS IN BIOPROCESSING II (eds. Todd, P. et al.), Amer. Chem. Soc., Washington, D.C., which is incorporated by reference herein. Additional pertinent publications include Spirin et al. (1988) Science 242: 1162–1164; Rattat et al. (1990) Tibtech 8: 275–276; Baranov et al. (1989) Gene 84: 463–466; Ryabova et al. (1989) Nucleic Acids Res. 17: 4412; and Kigawa et al. (1991) J. Biochem. (Tokyo) 110: 166–168, all of which are incorporated by reference herein.

Our preferred apparatus for continuous-flow cell-free methods according to this invention is a bottom-fed bioreactor such as is shown in FIG. 8 of Spirin, A. S. (1991) except without polysaccharide beads in the reactor. We prefer that the reactor be a chromatography micro-column equipped with an ultrafiltration membrane at the outlet (top) and a standard column adaptor at the bottom. We prefer that the column contain a thermostated water jacket to control the temperature. The reaction volume can be set by the adaptor so that no air is present within the column and a constant volume of liquid in the reactor can be maintained without difficulty. As indicated, the column is positioned "upside down" with the column adaptor at the bottom (inlet) and the membrane at the top (outlet). Relatively lighter feeding solution thus enters the heavier reaction mixture, sometimes called the incubation mixture, from the bottom and causes convection mixing in the column. The need for stirring is eliminated, and only one pump is required.

This invention also includes reagent kits for synthesizing proteins of the user's choice by transcription plus coupled replication-translation according to the methods of this invention. In a preferred embodiment the kit is for coupled transcription-replication-translation. The kit includes at least the following reagents:

1. a cell free translation system,
2. an RNA-directed RNA polymerase, preferably Qβ replicase,
3. a DNA-directed RNA polymerase, preferably a bacteriophage polymerase, and
4. a plasmid which serves as a template for the DNA-directed RNA polymerase for the synthesis of a replicatable mRNA that is compatible with the RNA-directed RNA polymerase, said plasmid containing a unique restriction site into which a messenger sequence for the user-selected protein can be cloned.

A kit according to the invention may optionally include one or more additional reagents, such as, for example, restriction enzymes, ribonucleoside triphosphates, and a radioactive amino acid.

BRIEF DESCRIPTION OF THE DRAWINGS

FIG. 1 (*b*) is an autoradiograph showing a thin-layer chromatography separation of butyryl chloramphenicol (Butyryl Cm) generated in enzymatic assays of certain of the examples.

FIG. 2 (*b*) shows the amount of protein synthesized as a function of the amount of initial recombinant mRNA in uncoupled translation reactions and coupled replication-translation reactions according to certain of the examples.

EXAMPLES

Figure 1A:
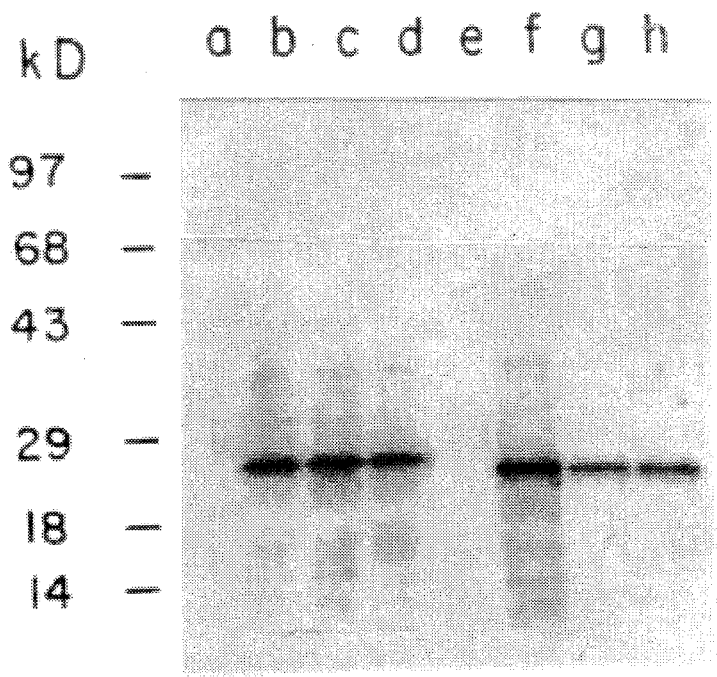
FIG. 1 (*a*) is an autoradiograph showing the electrophoretic mobility of proteins synthesized in certain of the examples.

The following examples illustrate preferred embodiments of the invention and do not limit the scope of the claims. In the examples, T7 RNA polymerase was purchased from Promega, and human placental ribonuclease inhibitor was purchased from Amersham. ATP, GTP, UTP, CTP, phosphoenol pyruvate and amino acids were purchased from Boehringer-Mannheim, [$^{35}$S]methionine (specific activity 170 Ci/mmol) and [$^3$]Leucine (specific activity 40 Ci/mmol) were obtained from "Isotope" (USSR), and [$^{14}$C]chloramphenicol (specific activity 57 mCi/mmol) was purchased from Amersham. An S-30 extract from *Escherichia coli* MRE-600 was prepared according to Chen and Zubay (1983) Methods Enzymol. 101: 674–690.

Example 1

Construction of Plasmids

A 783-basepair DNA segment, containing the entire sequence of *Escherichia coli* chloramphenicol acetyltransferase messenger RNA (CAT mRNA) (Close et al. (1982) Gene 20: 305–316) was cleaved from plasmid pCM-1 (Pharmacia) by digestion with endonuclease SalI (New England Biolabs) and cloned into the XhoI restriction site of the polylinker in plasmid pT7-MDV-poly (Lizardi et al. (1988) Biotechnology 6: 1197–1202), which is incorporated by reference herein. The criteria for determining where the XhoI restriction site was to be located were as follows. The inserted sequence should not significantly disturb the sequences and structures required for the replication of the recombinant transcript RNA. Insertion into hairpin loops located on the exterior of the molecule is preferred. Such loops can be ascertained by partial nuclease digestion experiments. Miele et al. (1983) J. Mol. Biol. 171: 281–295, which is incorporated by reference herein. They can also be estimated by computer programs that predict the secondary and tertiary structures that will be formed by an RNA molecule. Construction and trial of a plasmid to confirm its satisfactory operation is routine. Two different recombinant plasmids were isolated. One, pT7-MDV(+)CAT(+), contained the CAT sequence in the orientation that gives rise to transcripts that contain CAT mRNA embedded within MDV-1 (+) RNA. The other, pT7-MDV(+)CAT(−), gives rise to transcripts that contain the complement of the CAT sequence embedded within MVD-1 (+) RNA.

Example 2

Preparation of Plasmid DNA

Preparative amounts of plasmid DNAs were isolated by the alkaline method according to Birnboim and Doly (1979) Nucleic Acids Res. 7: 1513–1525, which is incorporated herein by reference, with subsequent gel-filtration through Sephacryl S1000 (Pharmacia).

Example 3

Transcription

Prior to transcription, plasmid pT7-MDV(+)CAT(+) or pT7-MDV(+)CAT(−) was digested with endonuclease SmaI (New England Biolabs). 5 µg of linearized plasmid were incubated with 100 units of bacteriophage T7 RNA polymerase (New England Biolabs) for 2 hours at 37° C. in 75 µl of 4 mM ATP, 4 mM CTP or [α–$^{32}$P]CTP, 4 mM GTP, 4 mM UTP, 15 mM MgCl$_2$, 90 mM Tris-HCl (pH 7.8), and 75 units of the ribonuclease inhibitor, RNasin (Promega). The reaction mixture was then incubated with 15 units of ribonuclease-free deoxyribonuclease I (Boehringer) at 37° C. for 30 minutes to destroy the template DNA. The transcripts were then purified by phenol/chloroform/isoamyl alcohol extraction, followed by precipitation with ethanol. The concentration of labeled RNA was determined from its specific radioactivity, and its size and homogeneity were determined by electrophoresis through a denaturing 4% polyacrylamide gel (containing 8M urea) that was visualized by autoradiography. The concentration of unlabeled RNA was determined from its absorption at 260 nm, and its size and homogeneity were determined by electrophoresis through a 1% agarose gel that was visualized by staining with ethidium bromide.

Example 4

CAT Activity Assays

35-µl samples from a cell-free protein synthesis reaction were analyzed. 5.4 µg of [$^{14}$C]chloramphenicol (Amersham) and 25 µg of n-butyryl coenzyme A (Promega) were added to each sample, the buffer was brought to 180 mM Tris-HCl (pH 8), the volume was adjusted to 125 µl, and incubation was carried out at 37° C. for 3 hr (Rosenthal (1987) Meth. Enzymol. 152: 704–720). Chloramphenicol and butyrylated chloramphenicol were extracted from the reaction mixture with 500 µl of ethyl acetate, transferred to another tube, dried by evaporation, resuspended in 20 µl of ethyl acetate, spotted onto a Polygram SIL G/UV silica gel thin-layer-chromatography plate (Macherey-Nagel), separated by developing the plate in 97:3 chloroform:methanol (vol/vol) for 1 hr, air dried, and then visualized by autoradiography.

Example 5

Coupled and Uncoupled Batch Translations

Eight different cell-free translations were carried out in batch as described using recombinant acetyltransferase mRNAs and using plasmids encoding recombinant chloramphenicol acetyltransferase prepared as described in Examples 1–3:

a. translation of MDV(+)CAT(−) transcript RNA;

b. coupled replication-translation according to this invention initiated with MDV(+)CAT(−) transcript RNA;

c. translation of MDV(+)CAT(+) transcript RNA;

d. coupled replication-translation according to this invention initiated with MDV(+)CAT(+) transcript RNA;

e. coupled transcription-translation initiated with linearized pT7-MDV(+)CAT(−) DNA;

f. coupled transcription-replication-translation according to this invention initiated with linearized pT7-MDV(+) CAT(−) DNA;

g. coupled transcription-translation initiated with linearized pT7-MDV(+)CAT(+) DNA; and h. coupled transcription-replication-translation according to this invention initiated with linearized pT7-MDV(+) CAT(+) DNA.

All eight reactions were incubated at 37° C. for 60 min in a 30 µl volume of 50 mM Tris-HCl (pH 7.4) containing 5 µl *E. coli* S-30 extract (Chen and Zubay (1983) Methods Enzymol. 101: 674–690), 10 µg *E. coli* tRNA, 300 ng pyruvate kinase (500 units/mg), 15 units human placental ribonuclease inhibitor, 100 mM potassium acetate, 12 mM magnesium acetate, 100 µm EDTA, 10 mM phosphoenol pyruvate, 500 mM ATP, 500 mM GTP, 20 mM dithiothreitol, 25 µM [$^{35}$S]methionine, and 25 µM of each of the other 19 amino acids. In addition, the uncoupled translation reactions (a and c) contained 6 pmol of recombinant transcript RNA; the coupled replication-translation reactions (b and d) contained all of the components of the uncoupled translation reactions plus 500 µM CTP, 500 µM UTP and 2 µg Qβ replicase; the coupled transcription-translation reactions (e and g) contained all of the components of the coupled replication-translation reactions, except that they contained 1 µg of SmaI-linearized recombinant DNA and 160 units of T7 RNA polymerase instead of recombinant transcript RNA and Qβ replicase; and the coupled transcription-replication-translation reactions (f and h) contained all of the components of the coupled transcription-translation reactions plus 2 µg Qβ replicase.

Figure 1B:
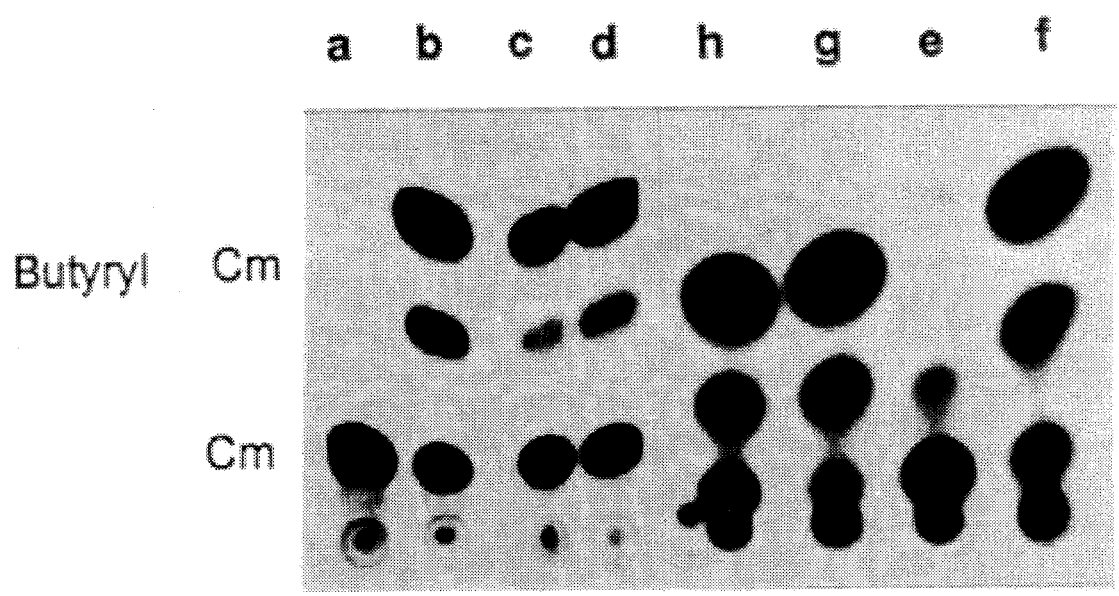

The protein products of the eight cell-free translations were analyzed. The size and homogeneity of the protein products were determined by electrophoresis through 10–25% polyacrylamide gels run in a denaturing buffer. Laemmli (1970) Nature 227: 680–685. The functional integrity of the protein products was determined by carrying out reactions to see whether the proteins could catalyze the acetylation of chloramphenicol, as described in Example 4. The results are shown in FIGS. 1 (a) and 1 (b). FIG. 1 (a) is an autoradiograph showing the electrophoretic mobility of the [$^{35}$S]proteins synthesized in each reaction in comparison to the mobility of marker proteins of known molecular mass. FIG. 1 (b) shows a thin-layer chromatography plate on which the butyrylated [$^{14}$C]chloramphenicol (Butyryl Cm) generated in each enzymatic assay was separated from the [$^{14}$C]chloramphenicol (Cm) precursor.

As shown in FIG. 1 (a) MDV(+)CAT(−) RNA did not serve as a template for protein synthesis in reaction a (translation) or reaction e (transcription-translation). This was as it should be. All other methods of this example resulted in synthesized protein, which in each case was virtually homogeneous and had a molecular mass and enzymatic activity characteristic of chloramphenicol acetyltransferase. The synthesis of functional protein in reactions in which the sense strand was generated by replication (reactions b and f) confirms that MDV(−)CAT(+) RNA can serve as a template for protein synthesis in coupled methods according to this invention. Replication functioned well with the E. coli extract, and translation occurred in coupled methods according to this invention.

Example 6

Continuous-Flow Coupled Replication-Translation

Continuous-flow cell-free replication-translation was carried out in an Amicon 8SC thermostat ed micro-ultrafiltration chamber containing an Amicon YM-100 ultrafiltration membrane (that nominally retains proteins with a molecular mass greater than 100 kilodaltons). The initial 1-ml solution in the chamber was 50 mM Tris-HCl (pH 7.4) containing 60 pmol MDV(+)CAT(−) transcript RNA, 80 µg Qβ replicase, 160 µl E. coli S-30 extract, 400 µg E. coli tRNA, 12 µg pyruvate kinase (500 units/mg), 400 units human placental ribonuclease inhibitor, 100 ng each of aprotinin, leupeptin, and chymostatin (to inhibit proteases), 12 µg folic acid, 100 mM potassium acetate, 12 mM magnesium acetate, 100 µM EDTA, 10 mM phosphoenol pyruvate, 500 mM ATP, 500 mM CTP, 500 mM GTP, 500 mM UTP, 20 mM dithiothreitol, 5 µM [$^3$H]leucine, and 20 µM of each of the other 19 amino acids. This solution was preincubated at 37° C. for 20 min. A feeding solution was then continuously pumped into the chamber at 1.6 ml/hr, while reaction products that passed through the ultrafilter were removed at the same rate. The feeding solution contained 50 mM Tris-HCl (pH 7.4), 100 mM potassium acetate, 12 mM magnesium acetate, 100 µM EDTA, 10 mM phosphoenol pyruvate, 500 mM ATP, 500 mM CTP, 500 mM GTP, 500 mM UTP, 20 mM dithiothreitol, 5 µM radioactively labeled amino acid (either [$^3$H]leucine or [$^{35}$S]methionine), and 20 µM of each of the other 19 amino acids. The reaction chamber was thermostated at 37° C. During the first five hours, and during the 19th to the 24th hour, the labeled amino acid was [$^{35}$S]methionine. At all other times, the labeled amino acid was [$^3$H]leucine. The amount of [$^3$H]leucine and [$^{35}$S]methionine incorporated into synthesized protein was determined by collecting two-hour fractions of the filtrate and measuring the radioactivity of the hot-trichloroacetic-acid-precipitable material with a dual-channel scintillation counter that discriminates between $^3$H and $^{35}$S. The size, homogeneity, and enzymatic activity of the synthesized protein in samples of the filtrate were determined as described in the legend to FIG. 1.

Example 7

Coupled Batch Replication-Translation Compared to Uncoupled Batch Translation

Using the reaction conditions of Example 5, four different cell-free translations in batch were carried out to compare the template efficiency of recombinant CAT mRNA during uncoupled translation and during coupled replication-translation according to this invention:

a. translation of MDV(+)CAT(−) transcript RNA;

b. coupled replication-translation initiated with MDV(+)CAT(−) transcript RNA;

c. translation of MDV(+)CAT(+) transcript RNA; and d. coupled replication-translation initiated with MDV(+)CAT(+) transcript RNA.

Figure 2A:
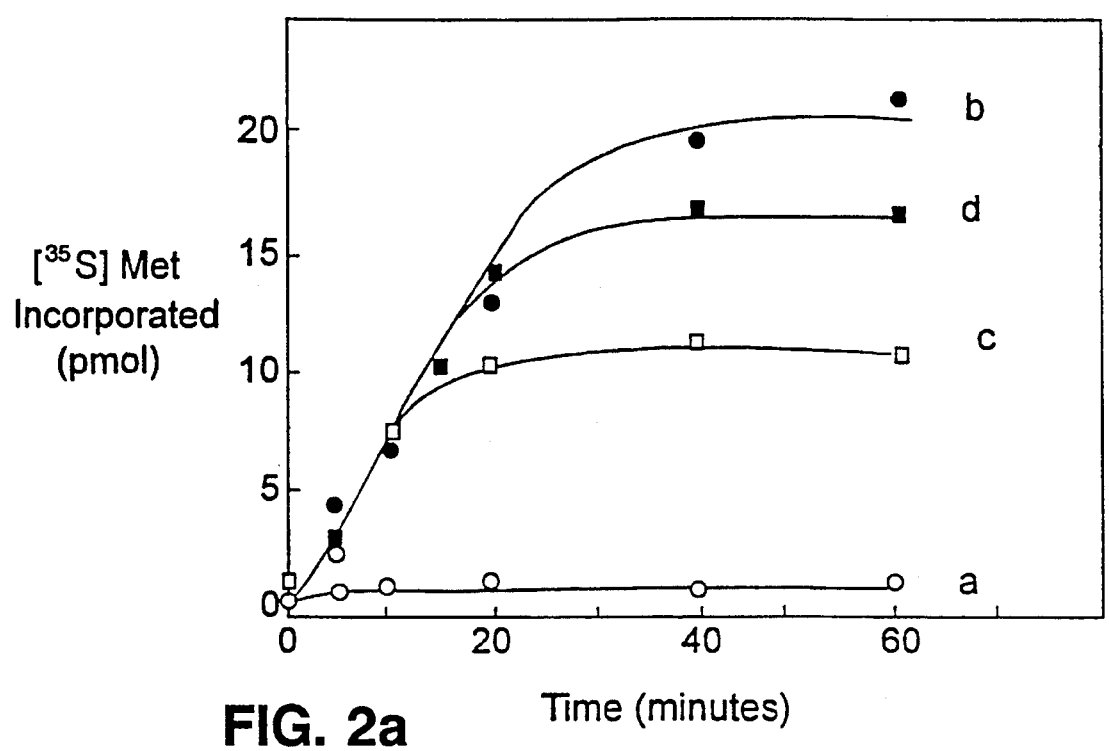
FIG. 2 (*a*) shows the kinetics of protein synthesis in uncoupled translation reactions and coupled replication-translation reactions according to certain of the examples.

The amount of [$^{35}$S]methionine incorporated into synthesized polypeptides was determined by sampling the reaction and measuring the radioactivity of the material that was precipitated in hot trichloroacetic acid. Mans and Novelli (1951) Arch. Biochem. Biophys. 94: 48–53. FIG. 2 (a) shows the amount of protein synthesized as a function of time of incubation in reactions initiated with 6 pmol of recombinant transcript RNA. FIG. 2 (b) shows the amount of protein synthesized after 60 minutes of incubation as a function of the amount of recombinant transcript RNA used to initiate the reactions.

Figure 2B:
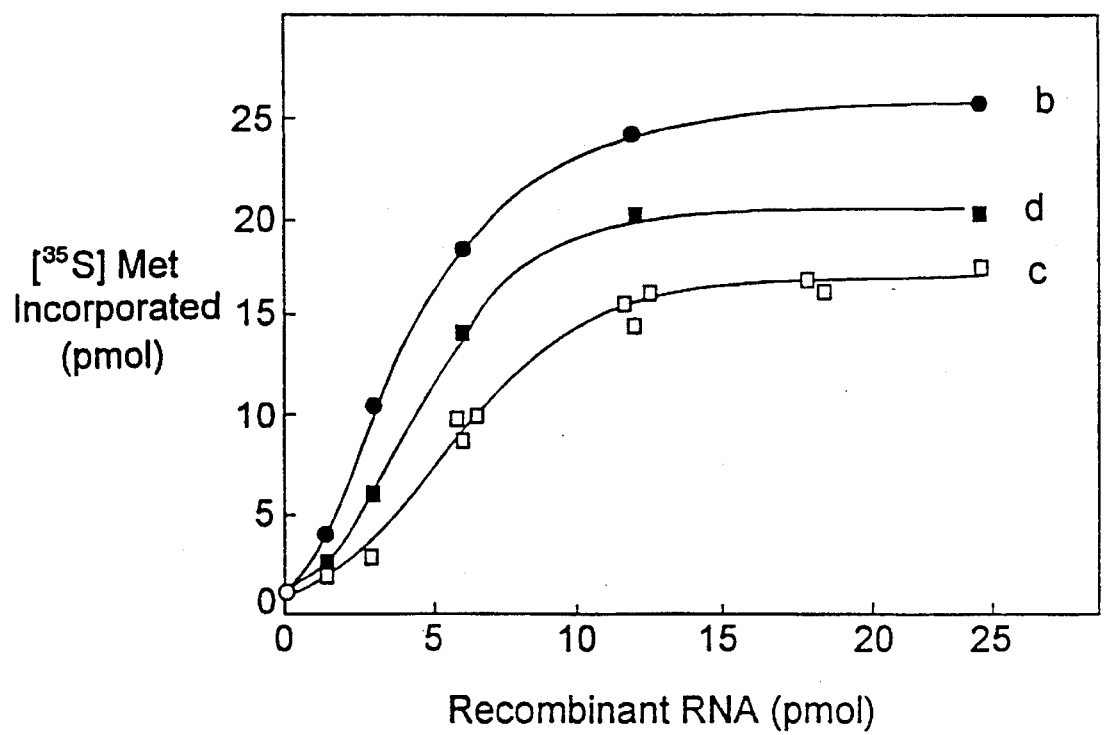

The results of this example were unexpected. FIG. 2 (a) shows a kinetic analysis of the amount of protein synthesized in replication-translation reactions initiated with recombinant transcript RNA, in comparison to the amount of protein synthesized in uncoupled translation reactions (which were identical except that they lacked Qβ replicase). More protein was synthesized in each of the coupled reactions than in the uncoupled reaction initiated with MDV(+)CAT(+) RNA. This result could be explained by the synthesis of additional template RNA by Qβ replicase in the coupled reactions. However, this is only a part of the explanation. FIG. 2(b) shows the dependence of the amount of protein synthesized in replication-translation reactions on the initial amount of recombinant transcript RNA, in comparison to the dependence seen in the uncoupled translation reactions initiated with MDV(+)CAT(+) RNA. The range of initial RNA concentrations was chosen so that some of the data would reflect the situation that occurs when there is so much template RNA available that it exceeds the number of ribosomes available to translate it, and the synthesis of additional RNA would have no effect on the amount of protein synthesized. The saturation of the ribosomes with recombinant mRNA is seen as plateaus in the dependence curves. The surprising result is that, even at initial RNA concentrations that saturate the available ribosomes, the amount of protein synthesized in the coupled replication-translation reactions was greater than the amount of protein synthesized in the uncoupled translation reactions. This result indicates that the efficiency of translation of recombinant mRNA is intrinsically higher when translation is coupled to replication.

We theorize that in coupled replication-translation reactions ribosomes can initiate the synthesis of proteins on nascent RNA strands. In uncoupled translation reactions, only full-length recombinant messenger RNAs are available for translation. The G:C-rich phage-like sequences at the ends of recombinant mRNAs interact to form strong tertiary structures that may restrict the ability of ribosomes to bind to the protein synthesis initiation site (which is located within each molecule at the beginning of the messenger sequence). In coupled systems, on the other hand, ribosomes can readily access the protein synthesis initiation site, as soon as it appears on a growing sense strand. The same situation occurs in phage-infected bacteria, where ribosomes translate nascent viral RNA strands as they are being synthesized.

Example 8

Figure 3:
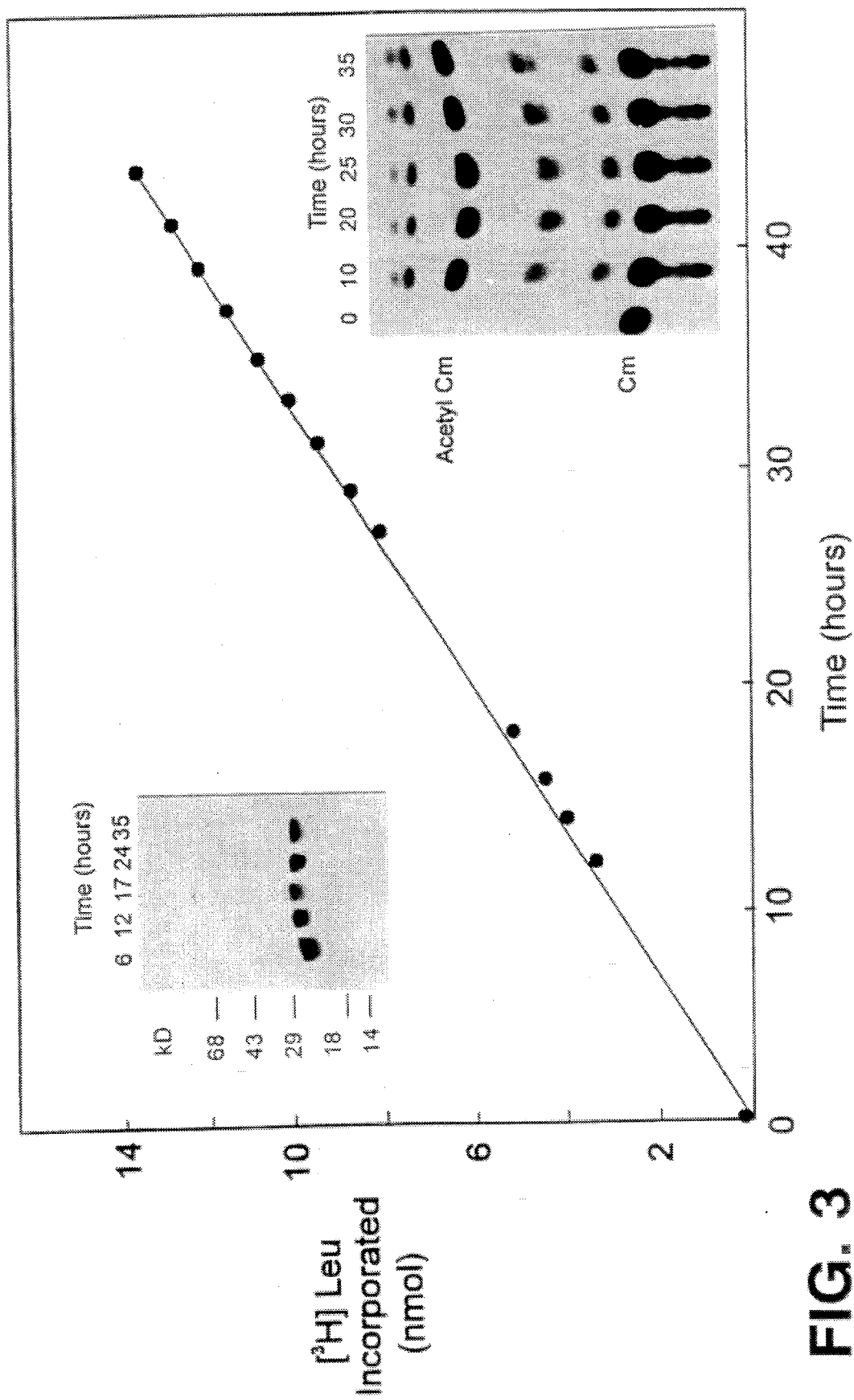
FIG. 3 shows the amount, size and homogeneity, and activity of protein made from recombinant chloramphenicol mRNA in a continuous-flow cell-free reactor according to Examples 6 and 8.

Continuous Synthesis of Biologically Active Chloramphicol Acetyltransferase in a Coupled Continuous-Flow Replication-Translation Chloramphenicol acetyltransferase from recombinant CAT mRNA was synthesized by the continuous-flow cell-free method of Example 6. FIG. 3 shows graphically the total amount of [$^3$H]leucine incorporated into protein as a function of time of incubation. The inset at the top left of FIG. 3 is a fluorograph showing an electrophoretic determination of the size and homogeneity of the synthesized protein as a function of time of incubation. The inset at the bottom right of FIG. 3 is an autoradiograph showing a determination of the enzymatic activity of the synthesized protein as a function of time of incubation.

A continuous-flow translation system maintains initial conditions. In this format, all the components of the cell-free translation system are incubated within a chamber that is bounded by an ultrafiltration membrane. Amino acids, nucleotides, and other small molecules are continually pumped into the chamber, while reaction products (including the synthesized protein) are withdrawn through the membrane. The macromolecular components of the translation system, including the ribosomes, the messenger RNA, the soluble enzymes, and the transfer RNAs, are retained within the chamber, perhaps because they are associated with molecular complexes that are too large to pass through the pores of the membrane. Spirin, A. S. in Frontiers in Bioprocessing II (Todd et al., eds.) 31–43 (American Chemical Society, Washington, D.C., 1991). We believe that a coupled replication-translation reaction in a continuous-flow format is particularly advantageous, because damaged messenger RNAs are continually replaced by newly synthesized RNA strands. Moreover, the threat of contamination posed by small replicatable RNAs that occur in the environment (such as MDV-1 RNA or RQ135 RNA) (Chetverin et al. (1991) J. Mol. Biol. 222: 3–9), which is incorporated herein by reference, is markedly reduced, since these RNAs do not contain ribosome binding sites and are small enough to be swept out of the system by the cleansing flow of buffered substrates.

The coupled replication-translation reaction shown in FIG. 3 was initiated with a nonsaturating concentration of MDV(+)CAT(−) transcript RNA and was incubated in a continuous-flow format for 43 hours. Protein synthesis continued at a steady rate throughout the reaction. [$^3$H]leucine was present in the feeding solution, except during the first five hours and during the 19th to the 24th hour, when [$^{35}$S]methionine was present. We used this pulse-labeling scheme to confirm that the proteins seen in the filtrate resulted from de novo synthesis, rather than from the leakage of protein that had been synthesized at earlier times. An electrophoretic analysis of the protein synthesized at various times showed that it continued to be a virtually homogeneous protein of a size characteristic of chloramphenicol acetyltransferase (top inset in FIG. 3). Most significantly, an enzymatic assay of the protein synthesized at various times showed that it retained its characteristic biological activity (bottom inset in FIG. 3).

We were surprised that this continuous-flow replication-translation system worked so well. We had expected that the rate of protein synthesis would slow down as the reaction proceeded, due to the presence of the relatively unstructured heterologous sequence in the recombinant mRNA, which would cause accumulating complementary strands to hybridize to each other. The resulting double-stranded RNAs would not possess the structured ribosome binding site that is required for translation to take place. Moreover, we had expected that the enzymatic activity of the newly synthesized protein would diminish as the reaction proceeded, due to the accumulation of mutations in the messenger RNA, as the RNA population goes through many rounds of replication.

We theorize that the coupled replication-translation system works well in the continuous-flow format because it mimics the situation that occurs in a phage-infected cell. In the cell, sense strands (genomic strands) serve as templates for the expression of phage proteins. The attraction of ribosomes to the sense strands probably restricts the binding of the replicase. On the other hand, antisense strands do not possess ribosome binding sites, so they are free to bind to the replicase. Consequently, antisense strands are probably the main templates for the replicase, and many more sense strands are synthesized than antisense strands (which is exactly the desirable situation for the phage, since only sense strands are incorporated into progeny phage particles, and since only sense strands are needed to serve as templates for the synthesis of phage proteins). We predict that, had we examined the recombinant messenger RNA in the coupled replication-translation reaction, we would have seen a marked increase in the ratio of sense to antisense strands over time. As a consequence of this asymmetric synthesis, most of the sense strands remain unhybridized and are free to serve as templates for protein synthesis. Moreover, since only antisense strands are readily available as templates for RNA synthesis, very few new antisense strands are synthesized, and the same antisense strands are utilized over and over as templates for the synthesis of new sense strands, thus markedly reducing the occurrence of mutant messenger sequences in the RNA population.

Unlike the situation in phage-infected cells, the heterologous proteins synthesized from recombinant messenger RNAs in replication-translation systems have no regulatory effect on RNA synthesis or protein expression.

We feel that the most convenient means of synthesizing relatively large amounts of any desired polypeptide will be to use coupled transcription-replication-translation reactions that are carried out in a continuous-flow format. These reactions could be initiated with recombinant plasmids that encode an antisense transcript. Unlike coupled transcription-translation reactions (in which RNA synthesis comes to a halt after one or two hours), the presence of Qβ replicase ensures that new sense strands are continually synthesized, thus extending the period during which functional proteins can be synthesized to several days.

Example 9

Comparison of Coupled Batch
Transcription-Translation to Coupled Batch
Transcription-Replication-Translation Four cell-free batch translations were carried out according to Example 5 to compare the kinetics of coupled T7 transcription-translation with coupled T7 transcription-Qβ replication-translation according to this invention:

a. transcription-translation of 1 microgram of MDV(+)CAT(−) DNA;

b. transcription-translation of 1 microgram of MDV (+) CAT (+) DNA;

c. transcription-replication-translation of 1 microgram of MDV(+)CAT(−) DNA, according to this invention; and d. transcription-replication-translation of 1 microgram of MDV(+)CAT(+) DNA, according to this invention.

Figure 4:
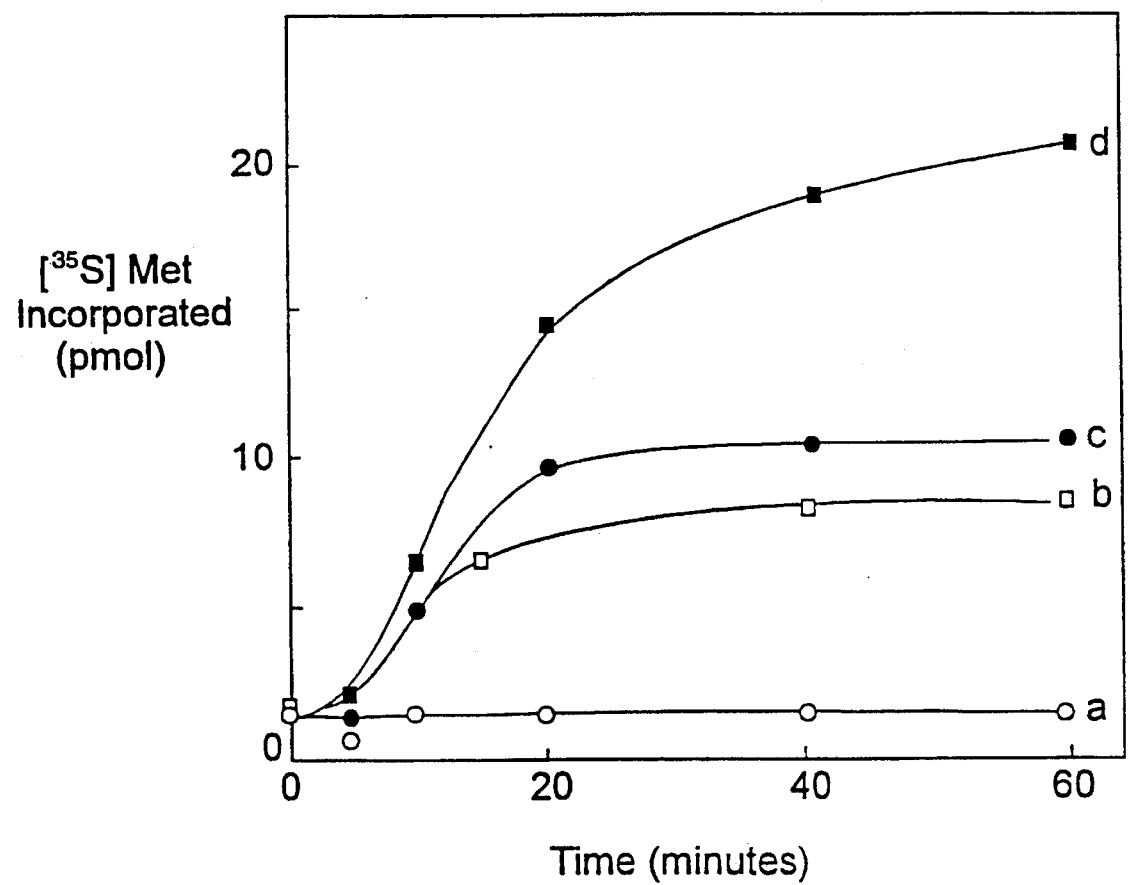
FIG. 4 shows the kinetics of protein synthesis in coupled transcription-translation reactions and coupled transcription-replication-translation reactions according to certain of the examples.

FIG. 4 shows the kinetics of incorporation of [$^{35}$S] methionine into protein for each reaction over a 60-minute incubation. We believe that in each reaction the amount of mRNA strands present exceeded the ribosomes present, i.e., the ribosomes were saturated by the mRNA.

Example 10

Coupled Replication-Translation of Recombinant
RNA Consisting of the Sequence of DHFR RNA
Embedded Within the Sequence of RQ135 RNA Starting with RQ135 RNA, another template for Qβ replicase, we can prepare recombinant mRNA that translates for *E. coli* dihydrofolate reductase (DHFR). RQ135 RNA has an attractive loop for insertion of mRNA sequences near the middle of the RQ135 sequence. See Munishkin et al. (1991) J. Mol. Biol. 221: 463–472, which is incorporated herein by reference. Plasmid preparation, transcription and replication proceed similarly to Examples 1–3. Coupled translations proceed similarly to Example 4 (batch) and Examples 6 and 8 (continuous). In a coupled replication-translation method according to this invention, biologically active DHFR is made.

We claim:

1. A coupled replication-translation process for the cell-free synthesis of protein comprising incubating in a single reaction vessel a. an RNA-directed RNA polymerase, a compatible veplicable recombinant mRNA, and ribonucleoside triphosphate precursors of RNA; and b. a cell-free translation system for protein synthesis.

2. The process according to claim 1 wherein the RNA-directed RNA polymerase is Qβ replicase.

3. The process according to claim 2 wherein the compatible recombinant mRNA is selected from the group consisting of MVD-1 RNA and RQ135 RNA.

4. The process according to claim 1 wherein said step of incubating in a single reaction vessel includes additionally:

c. a DNA-directed RNA polymerase; and d. a template for said DNA-directed RNA polymerase for the synthesis of said compatible recombinant mRNA.

5. The process according to claim 4 wherein the RNA-directed RNA polymerase is Qβ replicase.

6. The process according to claim 5 wherein the DNA-directed RNA polymerase is a bacteriophage polymerase.

7. The process according to claim 5 wherein the compatible recombinant mRNA is selected from the group consisting of MVD-1 RNA and RQ135 RNA.

8. The process according to claim 4 wherein said template is a plasmid containing a unique restriction site into which a DNA encoding an mRNA sequence has been cloned.

9. The process according to claim 8 wherein the RNA-directed RNA polymerase is Qβ replicase.

10. The process according to claim 4 wherein said step of incubating comprises incubating continuously in a continuous-flow cell-free process.

11. The process according to claim 10 wherein the RNA-directed RNA polymerase is Qβ replicase.

12. The process according to claim 11 wherein the step of continuously incubating is carried out for at least two days.

13. The process according to claim 11 wherein the DNA-directed RNA polymerase is a bacteriophage polymerase.

14. The process according to claim 11 wherein the compatible recombinant mRNA is selected from the group consisting of MVD-1 RNA and RQ135 RNA.

15. The process according to claim 10 wherein said template is a plasmid containing a unique restriction site into which a DNA encoding an mRNA sequence has been cloned.

16. The process according to claim 10 wherein said step of continuously incubating is carried out for at least two days.

17. The process according to claim 1 wherein said step of incubating comprises incubating continuously in a continuous-flow cell-free process.

18. The process according to claim 17 wherein the RNA-directed RNA polymerase is Qβ replicase.

19. The process according to claim 18 wherein the compatible recombinant mRNA is selected from the group consisting of MVD-1 RNA and RQ135 RNA.

20. The process according to claim 17 wherein said step of continuously incubating is carried out for at least two days.

21. In a continuous-flow cell-free translation process for synthesizing protein, the improvement comprising coupling translation with replicating a replicatable recombinant mRNA with a compatible RNA-directed RNA polymerase.

22. The process according to claim 21 wherein the RNA-directed RNA polymerase is Qβ replicase.

23. The process according to claim 22 wherein the recombinant mRNA is selected from the group consisting of MDV-1 RNA and RQ135 RNA.

24. In a continuous-flow cell-free transcription-translation process for synthesizing protein, wherein a template is transcribed by a DNA-directed RNA polymerase to produce mRNA which is translated to synthesize protein, the improvement comprising transcribing a template comprising a compatible replicatable recombinant mRNA and coupling therewith replicating said recombinant mRNA with a compatible RNA-directed RNA polymerase.

25. The process according to claim 24 wherein the RNA-directed RNA polymerase is Qβ replicase.

26. The process according to claim 25 wherein the recombinant mRNA is selected from the group consisting of MDV-1 RNA and RQ135 RNA.

27. The process according to claim 26 wherein transcription is transcription of a plasmid containing a restriction site into which a DNA encoding an mRNA sequence has been cloned, said transcription being accomplished by a DNA-directed RNA polymerase.

28. A kit of reagents for synthesizing a user-selected protein by transcription plus coupled replication-translation comprising the following reagents:
   a. a cell-free translation system;
   b. an RNA-directed RNA polymerase;
   c. a DNA-directed RNA polymerase; and
   d. a plasmid which serves as a template for the DNA-directed RNA polymerase for the synthesis of a replicatable mRNA that is compatible with the RNA-directed RNA polymerase, said plasmid containing a unique restriction site into which a DNA encoding an mRNA sequence for the user-selected protein can be cloned.

29. The kit according to claim 28 wherein the RNA-directed RNA polymerase is Qβ replicase.

30. The kit according to claim 28 wherein the DNA-directed RNA polymerase is a bacteriophage polymerase.

31. The kit according to claim 28 further comprising a restriction enzyme.

32. The kit according to claim 28 further comprising ribonucleoside triphosphates.

33. The kit according to claim 28 further comprising a radioactive amino acid.

34. The kit according to claim 28 for synthesizing user-selected protein by coupled transcription-replication-translation.

35. The kit according to claim 34 wherein the RNA-directed RNA polymerase is Qβ replicase.

36. The kit according to claim 34 wherein the DNA-directed RNA polymerase is a bacteriophage polymerase.

37. The kit according to claim 34 further comprising a restriction enzyme.

38. The process according to claim 6 wherein the bacteriophage polymerase is selected from the group consisting of T7 RNA polymerase and SP6 RNA polymerase.

39. The process according to claim 13 wherein the bacteriophage polymerase is selected from the group consisting of T7 RNA polymerase and SP6 RNA polymerase.

40. The kit according to claim 30 wherein the bacteriophage polymerase is selected from the group consisting of T7 RNA polymerase and SP6 RNA polymerase.

41. The kit according to claim 36 wherein the bacteriophage polymerase is selected from the group consisting of T7 RNA polymerase and SP6 RNA polymerase.

42. The process according to claim 4 wherein said template is a plasmid encoding a compatible replicatable recombinant RNA, said plasmid including a restriction site at or near the end of the end of the sequence encoding the replicatable RNA.

43. The process according to claim 10 wherein said template is a plasmid encoding a compatible replicatable recombinant RNA, said plasmid including a restriction site at or near the end of the end of the sequence encoding the replicatable RNA.

44. The process according to claim 26 wherein said template is a plasmid encoding a compatible replicatable recombinant RNA, said plasmid including a restriction site at or near the end of the end of the sequence encoding the replicatable RNA.

* * * * *